US010632015B2

(12) United States Patent
Prugue et al.

(10) Patent No.: US 10,632,015 B2
(45) Date of Patent: Apr. 28, 2020

(54) GOGGLES WITH INTERCHANGEABLE LOCKING STRAP

(71) Applicant: Bell Sports, Inc., Scotts Valley, CA (US)

(72) Inventors: Ximena Prugue, Santa Cruz, CA (US); David M. Thompson, Ben Lomond, CA (US)

(73) Assignee: Bell Sports, Inc., Scotts Valley, CA (US)

( * ) Notice: Subject to any disclaimer, the term of this patent is extended or adjusted under 35 U.S.C. 154(b) by 203 days.

(21) Appl. No.: 15/851,680

(22) Filed: Dec. 21, 2017

(65) Prior Publication Data

US 2019/0192347 A1    Jun. 27, 2019

(51) Int. Cl.
*A61F 9/02* (2006.01)

(52) U.S. Cl.
CPC ................... *A61F 9/027* (2013.01)

(58) Field of Classification Search
CPC ............................. A61F 9/027; A63B 33/002
USPC ...................................... 2/448, 450
See application file for complete search history.

(56) References Cited

U.S. PATENT DOCUMENTS

| | | | |
|---|---|---|---|
| 3,605,204 A * | 9/1971 | Amundsen | A44B 11/06 24/171 |
| 6,047,410 A | 4/2000 | Dondero | |
| 6,611,965 B1 | 9/2003 | Lee | |
| 6,694,532 B2 | 2/2004 | Chen | |
| 2005/0036103 A1 * | 2/2005 | Bloch | G02C 3/003 351/116 |
| 2005/0193478 A1 * | 9/2005 | Hussey | A61F 9/027 2/436 |
| 2010/0229292 A1 | 9/2010 | Tan | |
| 2017/0035614 A1 | 2/2017 | Tran | |

(Continued)

FOREIGN PATENT DOCUMENTS

TW    535815 U    1/2017

OTHER PUBLICATIONS

Yakaon Y Series Ski Goggles Snowboard Frameless Spherical UV400 Protection Anti-fog Detachable REVO Mirror Lens for Men and Women Skiing Snowboarding Source: https://www.amazon.com/YAKAON-Snowboard-Protection-Detachable-Snowboarding/dp/B016ZLCYHO Date Accessed: Sep. 9, 2017.

(Continued)

*Primary Examiner* — Katherine M Moran
(74) *Attorney, Agent, or Firm* — Amardeep S. Grewal; Gerard M. Donovan; Reed Smith LLP

(57) ABSTRACT

Goggles include a goggle frame, a goggle strap, and a goggle strap connector. The goggle strap has a direction of strap tension when the goggles are worn by a user. The goggle strap connector includes a female bracket and a male bracket. The female bracket is directly coupled to the goggle frame or the goggle strap, including first and second bracket walls, a channel defined between the bracket walls, projections, and recesses. The male bracket is configured to mateably couple to the female bracket, including a sliding bar and an enlarged bar end. First movement of the goggle strap in the strap tension direction may move at least one of the bar bumps of the enlarged bar end past at least one of the projections to position the at least one of the bar bumps within at least one of the recesses.

19 Claims, 9 Drawing Sheets

(56) References Cited

U.S. PATENT DOCUMENTS

2017/0216098 A1    8/2017   Li

OTHER PUBLICATIONS

Zionor Zionor Lagopus Snowmobile Snowboard Skate Ski Goggles with Detachable Lens, Lagopus XA Dark Brown Mirror Silver Source: http://www.webcortex.com/product_detail.php?id=SKUB01AZDVL2M Date Accessed: Sep. 9, 2017.

* cited by examiner

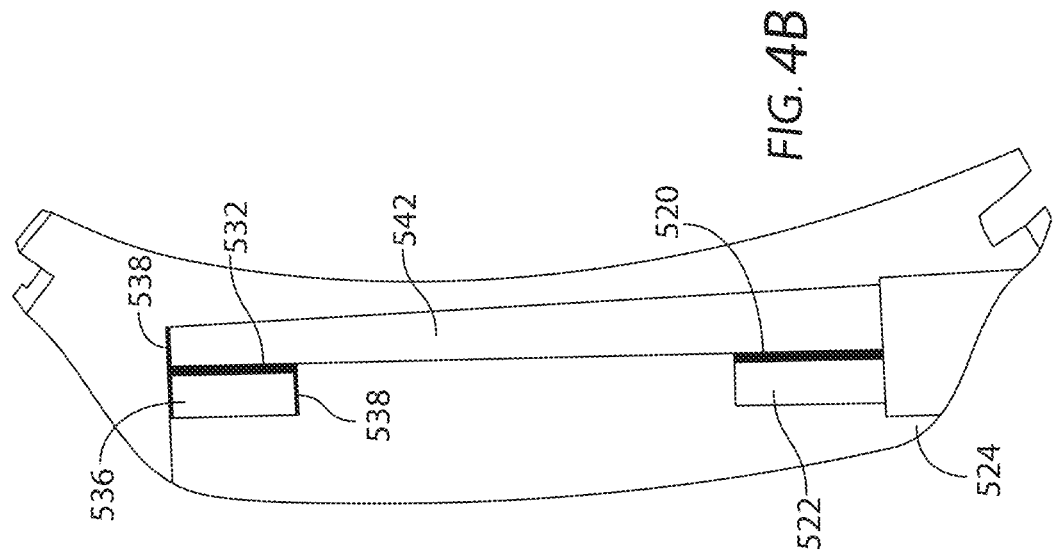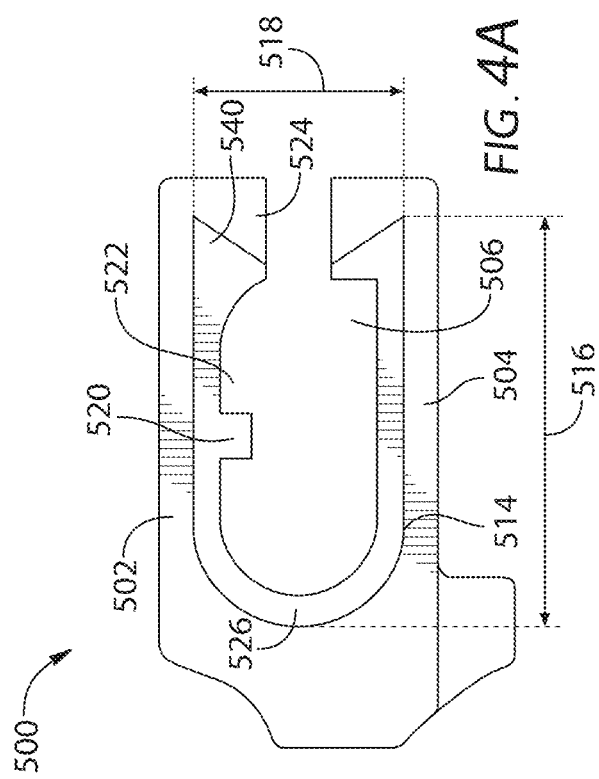

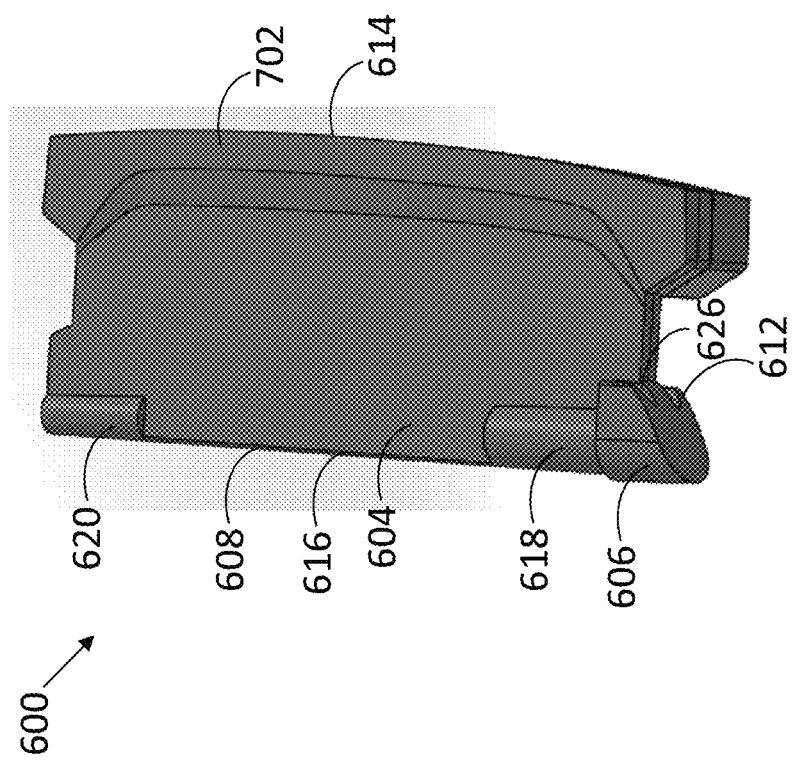

GOGGLES WITH INTERCHANGEABLE LOCKING STRAP

TECHNICAL FIELD

Aspects of this document relate generally to goggles, and more specifically to goggles comprising an interchangeable locking strap and methods of coupling a goggle strap to a goggle frame.

BACKGROUND

Goggles are desirable to have replaceable straps to extend the life of the goggles or to change the looks of the goggles. To connect a strap with the goggle frame of the goggles, a buckle-like structure is typically used. The buckle connects an end of the strap and is pushed and snapped into a receptor on the goggle frame. The buckle is immediately locked in the receptor once inserted into the space in the receptor. To disconnect, small parts are pushed or pressed to disengage the buckle from the goggle frame. A user often fumbles to find the right small parts to press or the right space to engage or disengage the buckle. The replacement of a goggle strap can be especially clumsy if the goggles are worn on the face of the user or the user has gloves on, and can consume precious time in time-pressured situations like in competitions or emergencies.

SUMMARY

According to an aspect of the disclosure, a pair of goggles comprises a goggle frame, at least one lens, a goggle strap, and a goggle strap connector. The goggle frame comprises two frame sides opposite each other. At least one lens aperture is defined by the goggle frame. At least one lens is mounted on the goggle frame, covering the at least one lens aperture. The goggle strap has two strap ends each having a direction of strap tension when the pair of goggles is worn by a user. The goggle strap connector is at each of the two frame sides. Each goggle strap connector respectively comprises a female bracket and a male bracket. The female bracket is coupled to the respective frame side and comprises a first bracket wall, a second bracket wall, a channel, one or more projections, one or more recesses, and an opposing pair of first teeth facing each other. The first bracket wall and the second bracket wall each extend away from the respective frame side. The channel may have a length greater than its width and its height, and is formed between the bracket walls. The channel has an opening end with an opening end height and an opening end width. The one or more projections may face the channel and extend into the channel from the first bracket wall. The one or more recesses on the first bracket wall are immediately adjacent to each of the one or more projections and distal to the respective frame side relative to the one or more projections. The opposing pair of first teeth each separately extends toward the respective frame side from a different wall of the first and second bracket walls. The pair of first teeth may be positioned distal to the respective frame side relative to the one or more recesses on the first bracket wall. The male bracket is on each of the two strap ends. Each male bracket respectively comprises a strap coupler, a sliding bar, an enlarged bar end, and an opposing pair of second teeth. The strap coupler is coupled to one of the two strap ends. The sliding bar extends from the strap coupler away from the goggle strap. The enlarged bar end is disposed on an edge of the sliding bar distal to the strap coupler. The enlarged bar end comprises one or more bar bumps along at least a portion of the edge of the sliding bar. The opposing pair of second teeth may face away from each other, each separately extending from the edge of the sliding bar toward the strap coupler. The opening end height and the opening end width of each channel is greater than a corresponding height and a corresponding width of the enlarged bar end to slidably receive the enlarged bar end into the channel. First movement of the male bracket within the channel in the strap tension direction may move at least one of the one or more bar bumps of the respective enlarged bar end past at least one of the one or more projections of the female bracket to position the at least one of the one or more bar bumps within the at least one of the one or more recesses and engage the pair of first teeth with the pair of second teeth.

Particular embodiments may comprise one or more of the following. The channel may comprise a closed end opposite the opening end of the channel. Second movement of the male bracket within the channel in a direction opposite the strap tension direction may move the at least one of the one or more bar bumps out of the at least one of the one or more recesses and past the at least one of the one or more projections. The first movement of the male bracket may produce a first click and the second movement of the male bracket may produce a second click. The one or more bar bumps may comprise a first bar bump proximal to the second teeth and a second bar bump disposed distal to the first bar bump on the sliding bar. The one or more projections may comprise a first projection proximal to the first teeth and a second projection distal to the opening end of the channel. The one or more recesses may comprise a first recess and a second recess. The enlarged bar end at the second bar bump may have a height greater than a height of the channel measured between the first bracket wall and the second bracket wall adjacent to the second recess, but smaller than a height of the channel measured between the first bracket wall and the second bracket wall at the second recess. The female bracket may further comprise a recess wall which extends into the channel from the first bracket wall or the second bracket wall and faces the channel, the recess wall not parallel to the second projection and disposed immediately adjacent to the second recess.

According to an aspect of the disclosure, a pair of goggles comprises a goggle frame comprising a first frame side, a goggle strap, and a goggle strap connector at the first frame side. The goggle strap has a first strap end, the first strap end having a direction of strap tension when the pair of goggles is worn by a user. The goggle strap connector comprises a female bracket and a male bracket. The female bracket is directly coupled to the first frame side or the first strap end. The female bracket comprises a first bracket wall, a second bracket wall, a channel defined between the bracket walls, one or more projections, and one or more recesses. The first bracket wall and the second bracket wall face each other and may be joined by a channel base. The channel may have a length greater than its width, the channel further having an opening end with an opening end height and an opening end width. The one or more projections may extend into the channel from the first bracket wall. The one or more recesses on the first bracket wall may be immediately adjacent to the one or more projections and distal to the channel base relative to the one or more projections. The male bracket is configured to mateably couple to the female bracket, comprising a sliding bar and an enlarged bar end. The sliding bar comprises a proximal end and a distal end, the proximal end directly coupled to the other of the first frame side or the first strap end that the female bracket is not directly coupled to.

The enlarged bar end is disposed on the sliding bar at the distal end, the enlarged bar end comprising one or more bar bumps along at least a portion of the sliding bar. The opening end height and the opening end width of the channel is greater than a corresponding height and a corresponding width of the enlarged bar end to slidably receive the enlarged bar end into the channel. First movement of the first strap end in the strap tension direction may move at least one of the one or more bar bumps of the enlarged bar end past at least one of the one or more projections of the female bracket to position the at least one of the one or more bumps within at least one of the one or more recesses and engage the male bracket with the female bracket.

Particular embodiments may comprise one or more of the following. The female bracket may comprise an opposing pair of first teeth facing each other and each separately extending toward the channel base from a different wall of the first and second bracket walls. The pair of first teeth may be positioned distal to the channel base relative to the one or more recesses on the first bracket wall. The male bracket may further comprise an opposing pair of second teeth facing away from each other and each separately extending from the enlarged bar end at the distal end of the sliding bar toward the proximal end. The first movement may move the at least one of the one or more bar bumps of the enlarged bar end past the at least one of the one or more projections to engage the pair of first teeth with the pair of second teeth. The channel may comprise a closed end opposite the opening end of the channel. Second movement of the male bracket within the channel, or the female bracket with the male bracket within the channel, in a direction opposite the strap tension direction may move the at least one of the one or more bumps out of the at least one of the one or more recesses and past the at least one of the one or more projections of the female bracket. The first movement may produce a first click. The second movement may produce a second click. The one or more bar bumps may comprise a first bar bump and a second bar bump disposed distal to the first bar bump on the sliding bar. The one or more projections may comprise a first projection proximal to the opening end and a second projection distal to the opening end of the channel. The one or more recesses may comprise a first recess and a second recess. The enlarged bar end at the second bar bump may have a height greater than a height of the channel measured between the first bracket wall and the second bracket wall adjacent to the second recess, but smaller than a height of the channel measured between the first bracket wall and the second bracket wall at the second recess. The first bar bump may be proximal to a pair of second teeth and the first projection may be proximal to a pair of first teeth. The female bracket may further comprise a recess wall which extends into the channel from the first bracket wall or the second bracket wall and faces the channel, the recess wall not parallel to the second projection and disposed immediately adjacent to the second recess.

According to an aspect of the disclosure, a method of coupling a goggle strap to a goggle frame comprises providing a goggle frame and a goggle strap. A female bracket is disposed on a first frame side of the goggle frame or a first end of the goggle strap. A male bracket is disposed on the first end of the goggle strap or the first frame side of the goggle frame. The goggle strap has a direction of strap tension when the goggle strap is pulled away from the strap end. The method further comprises slidably positioning an enlarged bar end of the male bracket into a channel of the female bracket through an opening end of the channel by sliding the enlarged bar end into the channel in a direction substantially perpendicular to the direction of strap tension. The method further comprises securing the male bracket to the female bracket by pulling the male bracket or the female bracket substantially parallel to the direction of strap tension after the enlarged bar end is positioned within the channel.

Particular embodiments may comprise one or more of the following. Securing the male bracket to the female bracket may further comprise moving one or more bar bumps of the enlarged bar end past one or more projections of the female bracket, and positioning the one or more bar bumps within the one or more recesses of the female bracket immediately adjacent to the one or more projections. Securing the male bracket to the female bracket may further comprise pulling the male bracket or the female bracket until a first click is produced. The method may further comprise unsecuring the male bracket from the female bracket by pushing the male bracket and the female bracket toward each other opposite the direction of strap tension until one or more bar bumps of the enlarged bar end disengage from one or more recesses, and sliding the enlarged bar end out of the channel in a direction substantially perpendicular to the direction of strap tension. Unsecuring the male bracket from the female bracket may further comprise pushing the male bracket and the female bracket toward each other until a second click is produced. Slidably positioning the enlarged bar end of the male bracket into the channel of the female bracket may further comprise slidably positioning the enlarged bar end of the male bracket into the channel of the female bracket until the enlarged bar end reaches a closed end of the channel opposite the opening end of the channel.

Aspects and applications of the disclosure presented here are described below in the drawings and detailed description. Unless specifically noted, it is intended that the words and phrases in the specification and the claims be given their plain, ordinary, and accustomed meaning to those of ordinary skill in the applicable arts. The inventors are fully aware that they can be their own lexicographers if desired. The inventors expressly elect, as their own lexicographers, to use only the plain and ordinary meaning of terms in the specification and claims unless they clearly state otherwise and then further, expressly set forth the "special" definition of that term and explain how it differs from the plain and ordinary meaning. Absent such clear statements of intent to apply a "special" definition, it is the inventors' intent and desire that the simple, plain, and ordinary meaning to the terms be applied to the interpretation of the specification and claims.

The inventors are also aware of the normal precepts of English grammar. Thus, if a noun, term, or phrase is intended to be further characterized, specified, or narrowed in some way, such noun, term, or phrase will expressly include additional adjectives, descriptive terms, or other modifiers in accordance with the normal precepts of English grammar. Absent the use of such adjectives, descriptive terms, or modifiers, it is the intent that such nouns, terms, or phrases be given their plain, and ordinary English meaning to those skilled in the applicable arts as set forth above.

Further, the inventors are fully informed of the standards and application of the special provisions of 35 U.S.C. § 112, ¶6. Thus, the use of the words "function," "means" or "step" in the Detailed Description or Description of the Drawings or claims is not intended to somehow indicate a desire to invoke the special provisions of 35 U.S.C. § 112, ¶6, to define the invention. To the contrary, if the provisions of 35 U.S.C. § 112, ¶6 are sought to be invoked to define the inventions, the claims will specifically and expressly state the exact phrases "means for" or "step for", and will also recite the word "function" (i.e., will state "means for performing the function of [insert function]"), without also reciting in such phrases any structure, material, or acts in support of the function. Thus, even when the claims recite a "means for performing the function of . . . " or "step for performing the function of . . . ," if the claims also recite any structure, material, or acts in support of that means or step, or to perform the recited function, it is the clear intention of the inventors not to invoke the provisions of 35 U.S.C. § 112, ¶6. Moreover, even if the provisions of 35 U.S.C. § 112, ¶6, are invoked to define the claimed aspects, it is intended that these aspects not be limited only to the specific structure, material, or acts that are described in the preferred embodiments, but in addition, include any and all structures, material, or acts that perform the claimed function as described in alternative embodiments or forms in the disclosure, or that are well-known present or later-developed, equivalent structures, material, or acts for performing the claimed function.

The foregoing and other aspects, features, and advantages will be apparent to those artisans of ordinary skill in the art from the DETAILED DESCRIPTION and DRAWINGS, and from the CLAIMS.

BRIEF DESCRIPTION OF THE DRAWINGS

Implementations will hereinafter be described in conjunction with the appended drawings, where like designations denote like elements, and:

FIG. 4A is a side view of the female bracket of the goggle strap connector shown in FIG. 3;

FIG. 4B is a sectional view of the female bracket shown in FIG. 3 as seen along section line 4B-4B of FIG. 3;

FIG. 5 is a top perspective view of the male bracket of the goggle strap connector shown in FIG. 3;

DETAILED DESCRIPTION

Figure 1A:
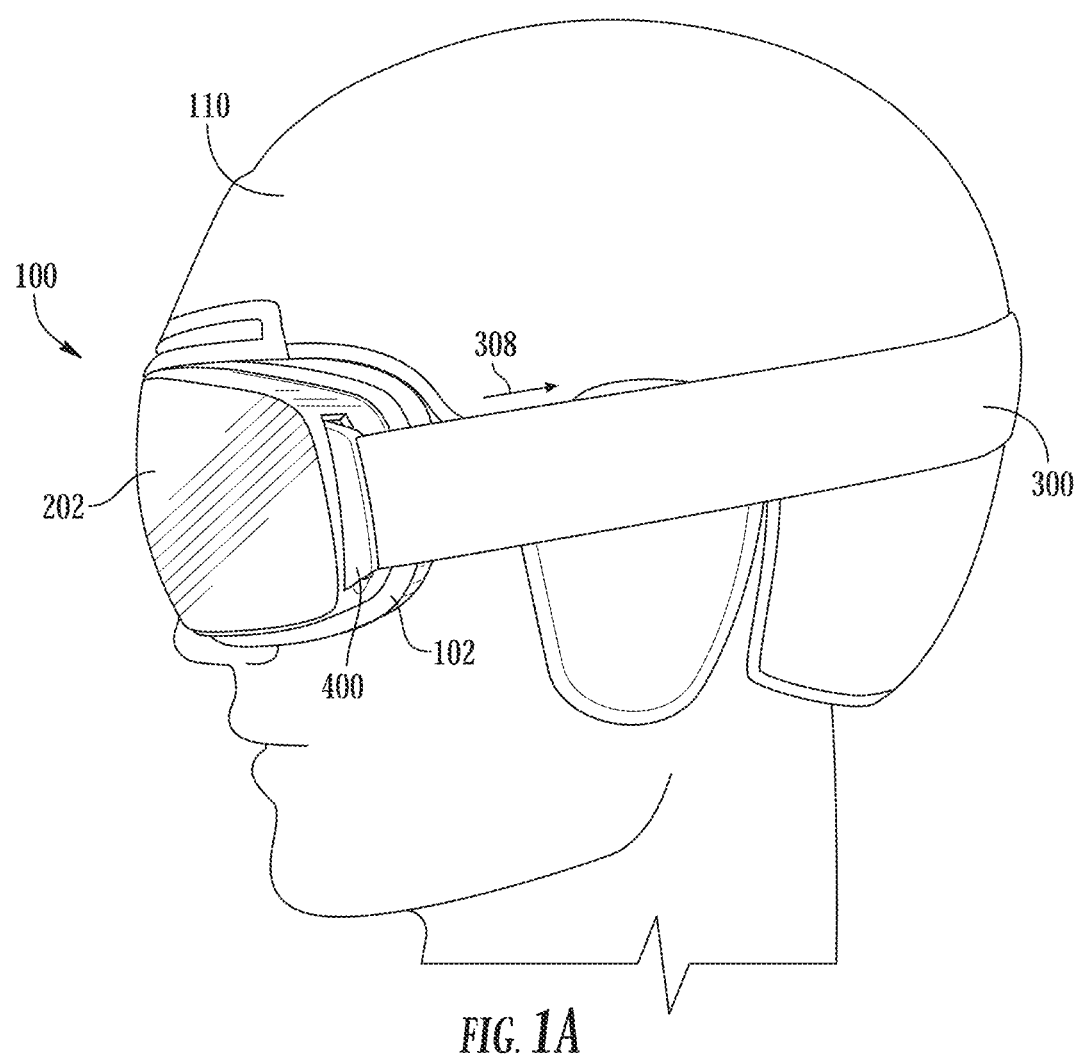
FIG. 1A is a side view of a pair of goggles worn on a user's head.

While this disclosure includes embodiments in many different forms, they are shown in the drawings and will herein be described in detailed particular embodiments with the understanding that the present disclosure is to be considered as an exemplification of the principles of the disclosed methods and systems, and is not intended to limit the broad aspect of the disclosed concepts to the embodiments illustrated.

Contemplated as part of this disclosure are goggles, of which the goggle strap is replaceable, as well as a method of coupling a goggle strap to a goggle frame. The assembly of the goggles allows the strap to be quickly and easily assembled onto, or dissembled from, the goggle frame, even with a gloved hand or while the goggles are worn on the user's face. Further, the locking direction of the goggle strap connector is the same as the strap tension direction, which helps the goggle strap connector stay locked while the goggles are worn on a user's head.

Figure 1B:
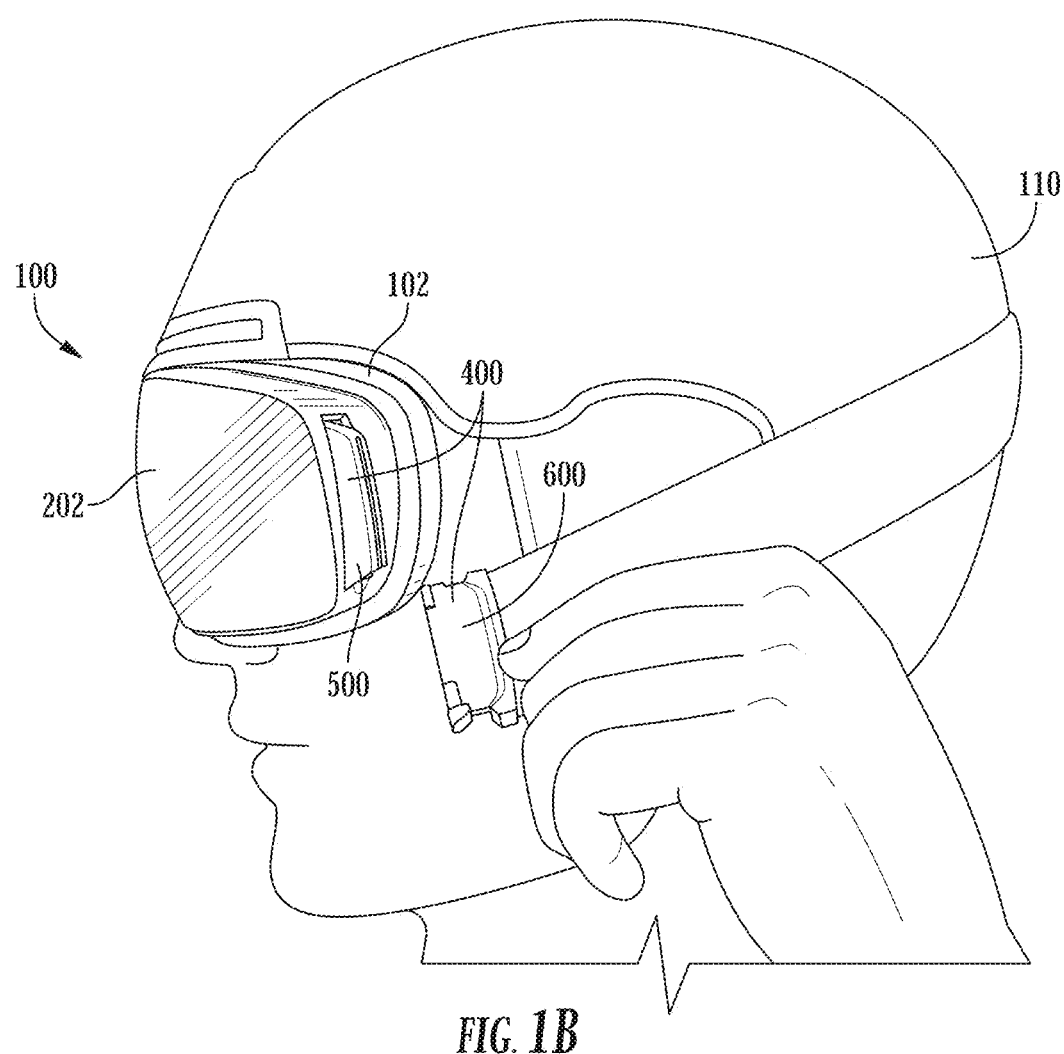
FIG. 1B is a side view of the pair of goggles shown in FIG. 1A with the goggle strap taken off one side of the goggle frame while the goggle frame remains on the user's head.

Goggles 100 comprise a goggle frame 102, a goggle strap or strap 300, and a goggle strap connector 400 connecting the goggle strap 300 with the goggle frame 102. FIG. 1A illustrates an example of goggles 100 worn on a user's head over a helmet 110. The goggles strap 300 can be taken off the goggle frame 102 even while the goggle frame 102 is on the user's face (FIG. 1B). In emergency situations, the goggles can, therefore, be easily taken off a user's face without first taking off the strap or the goggle frame or moving the user's head. This is beneficial for comfort and neck safety in an accident.

Figure 2:
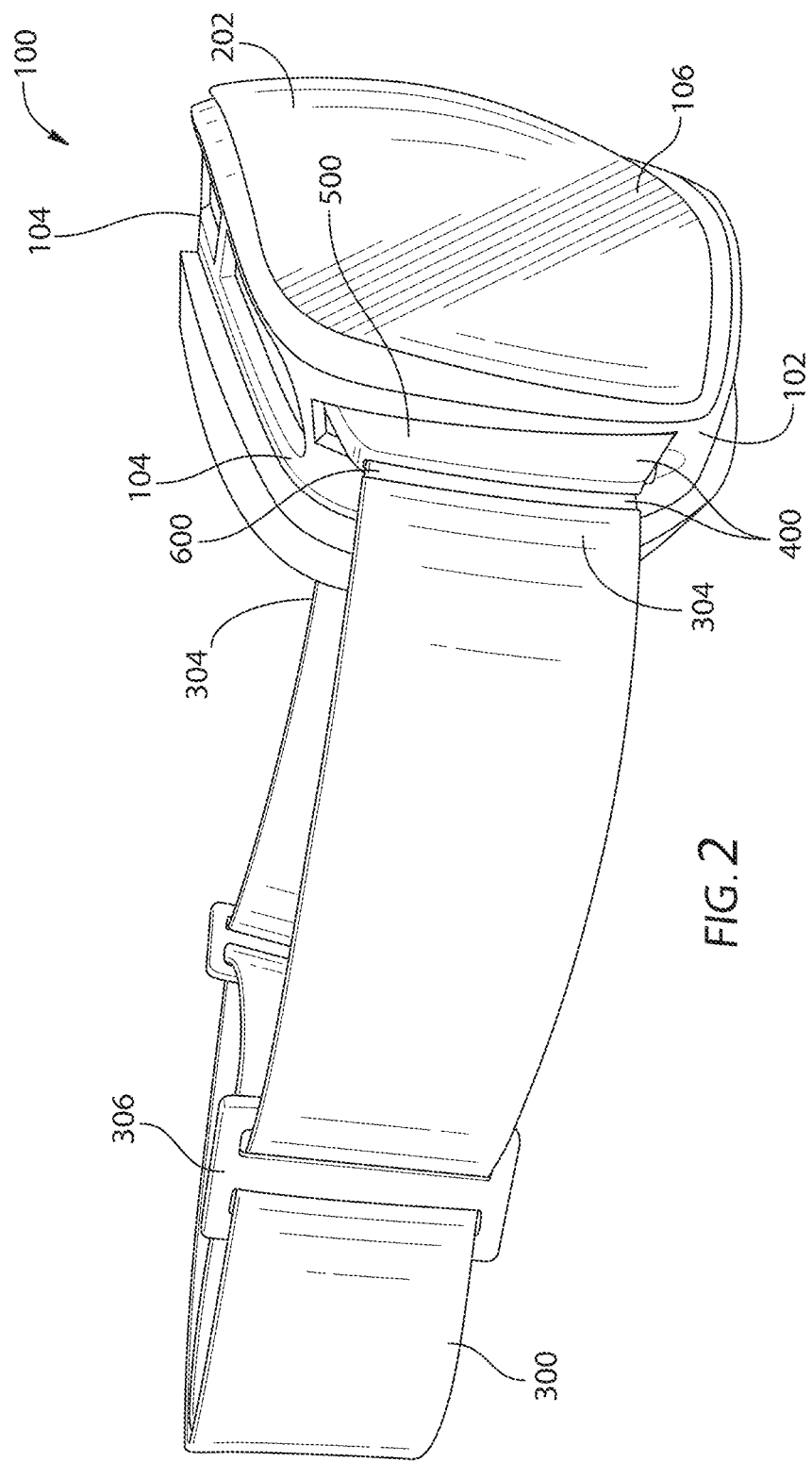
FIG. 2 is a side view of the goggles shown in FIG. 1A, separated from the helmet and user.

With reference to FIG. 2, at least one lens aperture 106 is defined by the goggle frame 102 with at least one lens 202 mounted on the goggle frame 102 and covering the at least one lens aperture 106. The goggle strap 300 comprises goggle strap ends 304 each with a direction of strap tension 308 when the goggles 100 are worn by a user (FIG. 1A). The goggle strap 300 may comprise a buckle 306 for adjusting the length of the goggle strap. Some goggles, such as those used in competitions, may not have a buckle.

Figure 3:
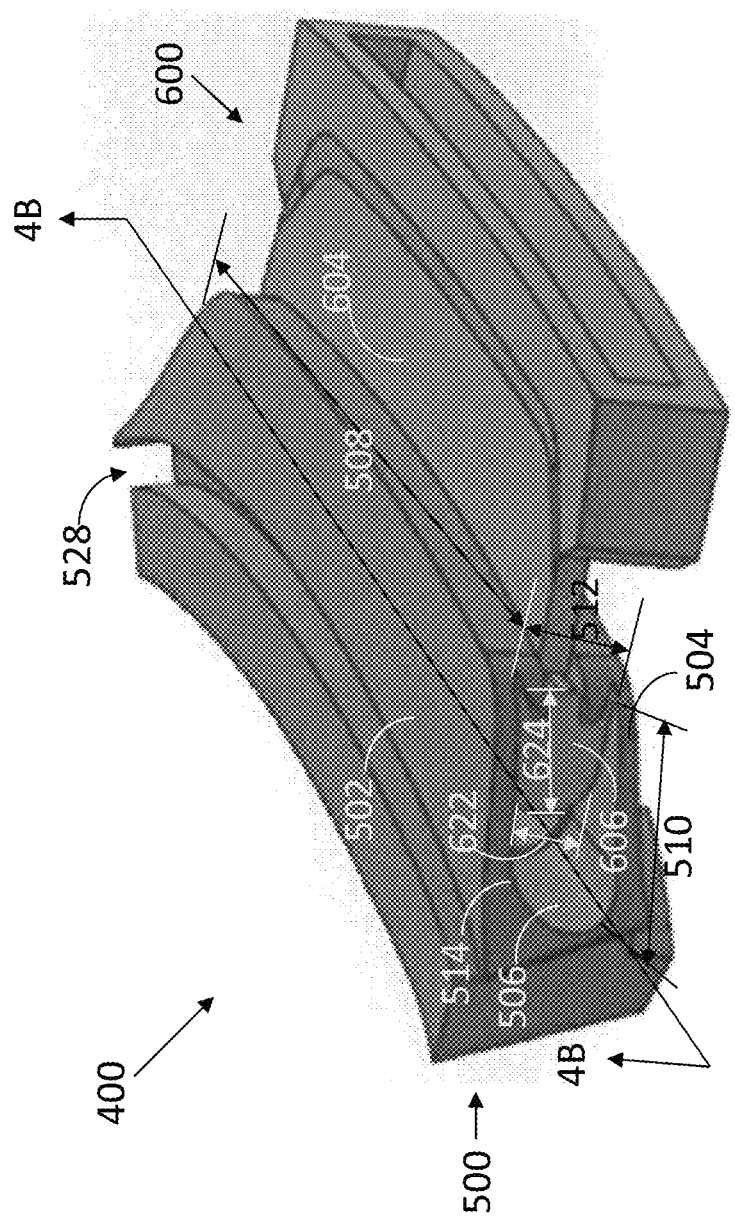
FIG. 3 is a side perspective view of a goggle strap connector.

The goggle strap connector 400 comprises a female bracket 500 and a male bracket 600 (FIG. 3). The male bracket 600 is configured to mateably couple to the female bracket 500. Although the goggles shown in FIGS. 1A-2 have the goggle strap 300 connected to the male bracket 600, the goggle strap 300 may alternatively be connected to the female bracket 500 with the male bracket 600 coupled with a frame side 104 of the goggle frame 102. The female bracket 500 is directly coupled to the frame side 104 or directly coupled to the goggle strap end 304, with the male bracket coupled to the other one of the frame side 104 or the goggle strap end 304. In some embodiments, the goggle strap connector 400 is at each of the two frame sides 104, and the female bracket 500 or the male bracket 600 is directly coupled to its respective frame side 104 with the male bracket 600 or the female bracket 500 directly coupled to each of the two strap ends 304 of the goggle strap 300.

With reference to FIGS. 3-4B, the female bracket 500 comprises a first bracket wall 502, a second bracket wall 504, a channel 506, one or more projections 520, and one or more recesses 522 (FIGS. 4A-4B). The first and second bracket walls 502 and 504 of the female bracket 500 face each other. The bracket walls 502 and 504 may be joined by a channel base 526. In some embodiments, the first and second bracket walls 502 and 504 extend away from the respective frame side 104 that the female bracket 500 coupled to. The channel 506 is defined by, or formed between, the first and second bracket walls 502 and 504. The channel 506 has a length 508 greater than its width 510 and a channel length 508 greater than its height 512. The width 510 and height 512 of the channel 506 shown in FIG. 3 are measured near the opening end 514. The width 510 or the height 512 may vary along the channel 506. The channel 506 has an opening end 514 with an opening end height 518 and an opening end width 516. The channel 506 may comprise a closed end 528 opposite the opening end 514 of the channel 506. The closed end 528 may help restrict the male bracket 600 from sliding too far into the channel 506.

One or more projections 520 in the female bracket 500 extends into the channel 506 from the first bracket wall 502. One or more recesses 522 on the first bracket wall 502 may be disposed immediately adjacent to the one or more projections 520 and distal to the channel base 526 relative to the one or more projections 520. In some embodiments, the one or more recesses 522 are disposed distal to the respective frame side 104 to which the female bracket 500 coupled, relative to the one or more projections 520. In some embodiments, the one or more recesses 522 are disposed distal to the channel base 526, relative to the one or more projections 520.

With reference to FIG. 5, the male bracket 600 comprises a sliding bar 604 and an enlarged bar end 606. The sliding bar 604 comprises a proximal end 614 and a distal end 616. The proximal end 614 may be directly coupled to the other of the goggle frame side 104 or the goggle strap end 304 that the female bracket 500 is not directly coupled to. The enlarged bar end 606 is disposed on the sliding bar 604 at the distal end 616. The enlarged bar end 606 comprises one or more bar bumps or bumps 618, 620 along at least a portion of the sliding bar 604.

In some embodiments, the male bracket 600 may be disposed on each of the two strap ends 304. The male bracket 600 may further comprise a strap coupler 702. The strap coupler 702 may be coupled to one of the two strap ends 304. The sliding bar 604 may extend from the strap coupler 702 away from the strap 300. The enlarged bar end 606 may be disposed on an edge 608 of the sliding bar 604 distal to the strap coupler 702. The bar bumps 618, 620 may be disposed along at least a portion of the edge 608 of the sliding bar 604.

Figure 6A:
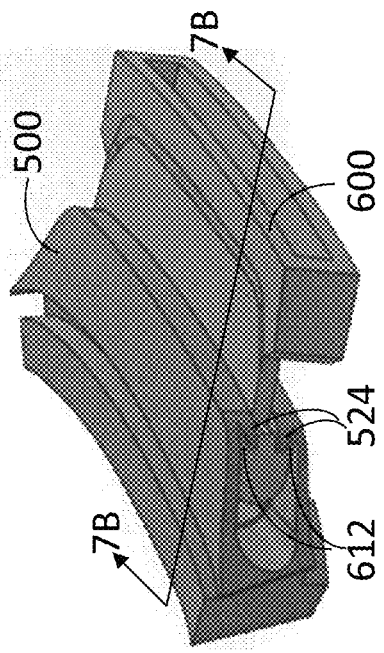
FIG. 6A is a side perspective view of the goggle strap connector shown in FIG. 3 with the enlarged end of the male bracket partially inserted in the channel of the female bracket.
Figure 6B:
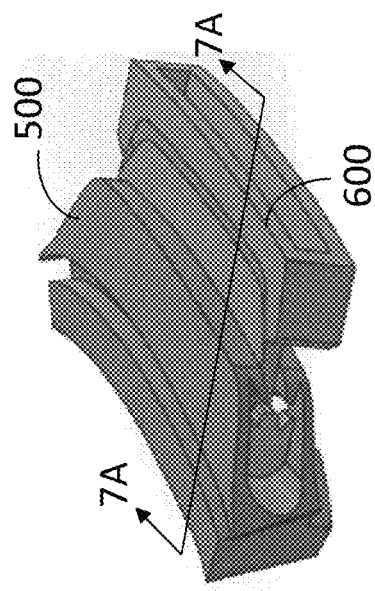
FIG. 6B is a side perspective view of the goggle strap connector shown in FIG. 3 with the enlarged end of the male bracket fully inserted in the channel of the female bracket.
Figure 6C:
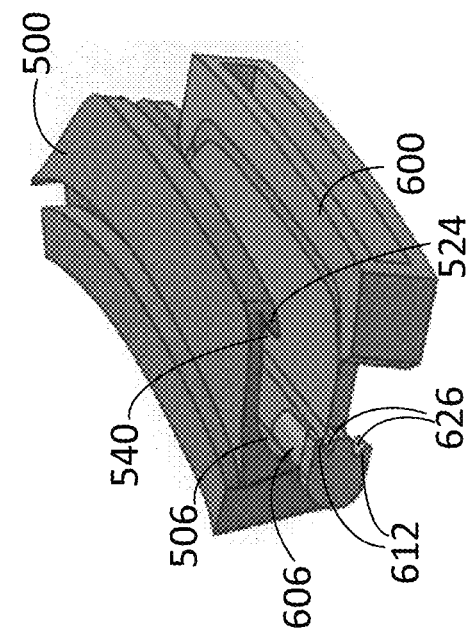
FIG. 6C is a side perspective view of the goggle strap connector shown in FIG. 3 with the female bracket and the male bracket engaged with each other.
Figure 7A:
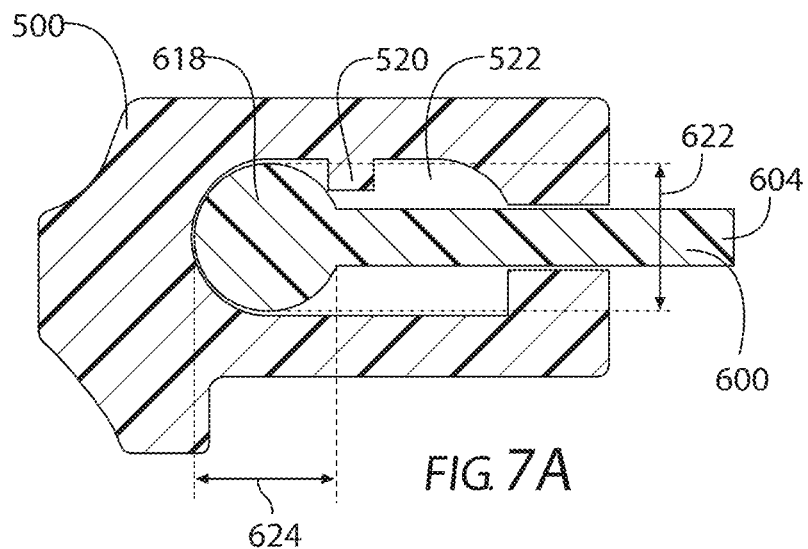
FIG. 7A is a sectional view of the goggle strap connector taken along section line 7A-7A shown in FIG. 6B.
Figure 7B:
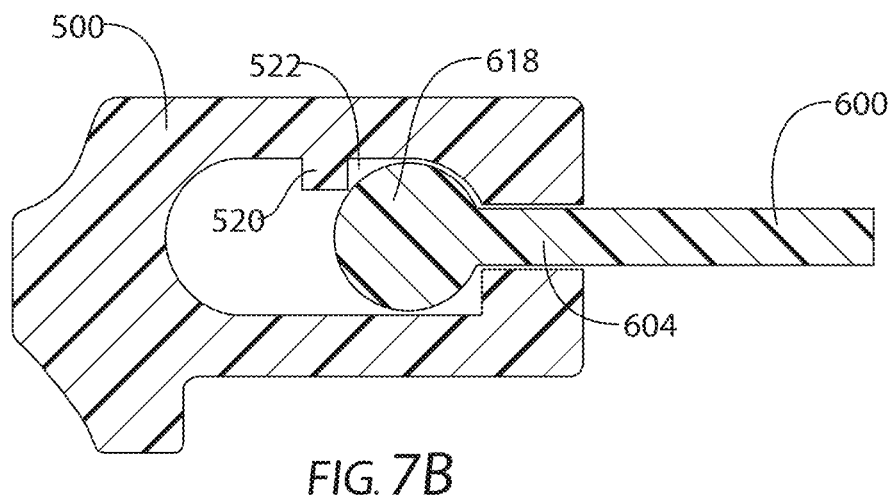
FIG. 7B is a sectional view of the goggle strap connector taken along section line 7B-7B shown in FIG. 6C.

The opening end height 518 and the opening end width 516 of the channel 506 of the female bracket 500 is greater than a corresponding height 622 and a corresponding width 624 of the enlarged bar end 606 to slidably receive the enlarged bar end 606 into the channel 506. To engage the female bracket 500 and the male bracket 600 with each other, the enlarged bar end 606 of the male bracket 600 first is inserted into the channel 506 of the female bracket 500, or the female bracket 500 is slid over the enlarged bar end 606, to position the enlarged bar end 606 into the channel 506 (FIGS. 6A-6B and 7A). A first movement of the first goggle strap end 304 in the strap tension direction then moves at least one of the one or more bar bumps 618, 620 of the enlarged bar end 606 past at least one of the one or more projections 520 of the female bracket 500 to position the at least one of the one or more bumps within the at least one of the one or more recesses 522 and engage the male bracket 600 within the female bracket 500 (FIGS. 6C and 7B). In some embodiments, the female bracket is coupled to a frame side and, during the first movement, the male bracket is moved within the channel in the strap tension direction. In other embodiments, the male bracket is couple to a frame side and, during the first movement, the female bracket is moved, with the male bracket within the channel, in the strap tension direction.

To disengage the female bracket 500 and the male bracket 600 from each other, a second movement of the male bracket 600 within the channel 506, or the female bracket 500 with the male bracket 600 within the channel 506, in a direction opposite the strap tension direction 308 moves the at least one of the one or more bumps out of the at least one of the one or more recesses 522 and past the at least one of the one or more projections 520 of the female bracket 500 (FIGS. 6B and 7A). The first movement may produce a first click. The second movement may produce a second click. As a result, the female bracket 500 and the male bracket 600 can be easily engaged and disengaged from each other, with an audible indication of engagement and disengagement, even when the user is wearing gloves. As a result, the female and male brackets, 500 and 600, are securely locked with each other when the goggles are worn on the user's head because the strap tension direction is the same as the locking direction. In some conventional replaceable goggles, the direction of strap tension pulls the strap away from the locking position.

The female bracket 500 may further comprise an opposing pair of first teeth 524 facing each other. Each of the first teeth 524 separately extend toward the channel base 526 from a different wall of the first and second bracket walls 502 and 504 and are positioned distal to the channel base 526 relative to the one or more recesses 522 on the first bracket wall 502. In some embodiments, each of the first teeth 524 may separately extend toward the respective frame side 104 to which the female bracket 500 is coupled, from a different wall of the first and second bracket walls 502 and 504. The first teeth 524 may be positioned distal to the respective frame side 104 relative to the one or more recesses 522 on a respective bracket wall 502 and 504. In some embodiments, each tooth of the pair of first teeth 524 and its respective bracket wall 502 or 504 forms a wall slot 540 between them extending along at least a portion of the channel 506.

The male bracket 600 may further comprise an opposing pair of second teeth 612 facing away from each other. Each of the second teeth 612 separately extends from the enlarged end 606 at the distal end 616 of the sliding bar 604 toward the proximal end 614. In some embodiments, the second teeth 612 may each separately extend from the edge 608 of the sliding bar 604 toward the strap coupler 702. The first movement moves at least one of the one or more bar bumps 618, 620 of the enlarged bar end 606 past the one or more projections 520 to engage the pair of first teeth 524 with the pair of second teeth 612. In some embodiments, each tooth 612 of the pair of second teeth 612 forms an end slot 626 between the respective tooth 612 and sliding bar 604. When the pair of first teeth 524 engage with the pair of second teeth 612, each tooth 524 of the pair of first teeth 524 is disposed in a respective end slot 626 and each tooth 612 of the pair of second teeth 612 is disposed in a respective wall slot 540. The first and second teeth 524 and 612 limit further movement of the enlarged bar end 606 of the male bracket 600 once the at least one of the one or more bar bumps 618, 620 engages in the at least one of the one or more recesses 522 during the first movement. The engagement of the teeth 524, 612 helps to restrict the enlarged bar end 606 from being overpulled out of the channel 506 of the female bracket 500 in the direction of strap tension 308 (FIG. 1).

The one or more bar bumps 618, 620 of the male bracket 600 may comprise a first bar bump 618 and a second bar bump 620 disposed distal to the first bar bump 618 on the sliding bar 604. The first bar bump 618 may be disposed proximal to the second teeth 612. As illustrated in the embodiment of FIG. 4B, the female bracket 500 may further comprise a continuous slide guide 542 disposed along the channel 506. The slide guide 542 is sized with dimensions greater than the respective dimensions of the bar bumps 618, 620 so the enlarged bar end 606 can be slid into the channel 506 along the slide guide 542.

With reference to FIGS. 4A and 4B, the one or more projections of the female bracket 500 may comprise a first projection 520 proximal to the opening end 514 of the channel 506 and a second projection 532 distal to the opening end 514. The first projection 520 may be proximal to the first teeth 524. The one or more recesses may comprise a first recess 522 and a second recess 536. The enlarged bar end 606 at the second bar bump 620 has a height greater than a height of the channel 506 measured between the first bracket wall 502 and the second bracket wall 504 adjacent to the second recess 536, but smaller than a height of the channel 506 measured between the first bracket wall 502 and the second bracket wall 504 at the second recess 536. As a result, when the strap 300 is pulled in the strap tension direction 308 during the first movement, this first movement moves at least one of the bar bumps 618, 620 past at least one of the one or more projections 520, 532 to position the at least one of the one or more bumps within at least one of the one or more recesses 522, 536 and engage the male bracket 600 with the female bracket 500.

In some embodiments, the female bracket 500 may further comprise a recess wall 538 which extends into the channel 506 from the first bracket wall 502 or the second bracket wall 504 and faces the second recess 536. The recess wall 538 adjacent the second projection 532 restricts the second bar bump 620 from sliding backwards toward the opening end 514 and, therefore, restricts the enlarged bar end 606 from slipping out of the channel 506 when the male and female brackets 600 and 500 are engaged with each other.

The goggle strap connector may be in-molded with the goggle frame, or ultrasonically welded, or even over-molded with silicon. In some embodiments, the goggle strap connector may be formed separate from the goggle frame and detachably coupled to the goggle frame.

Figure 8:
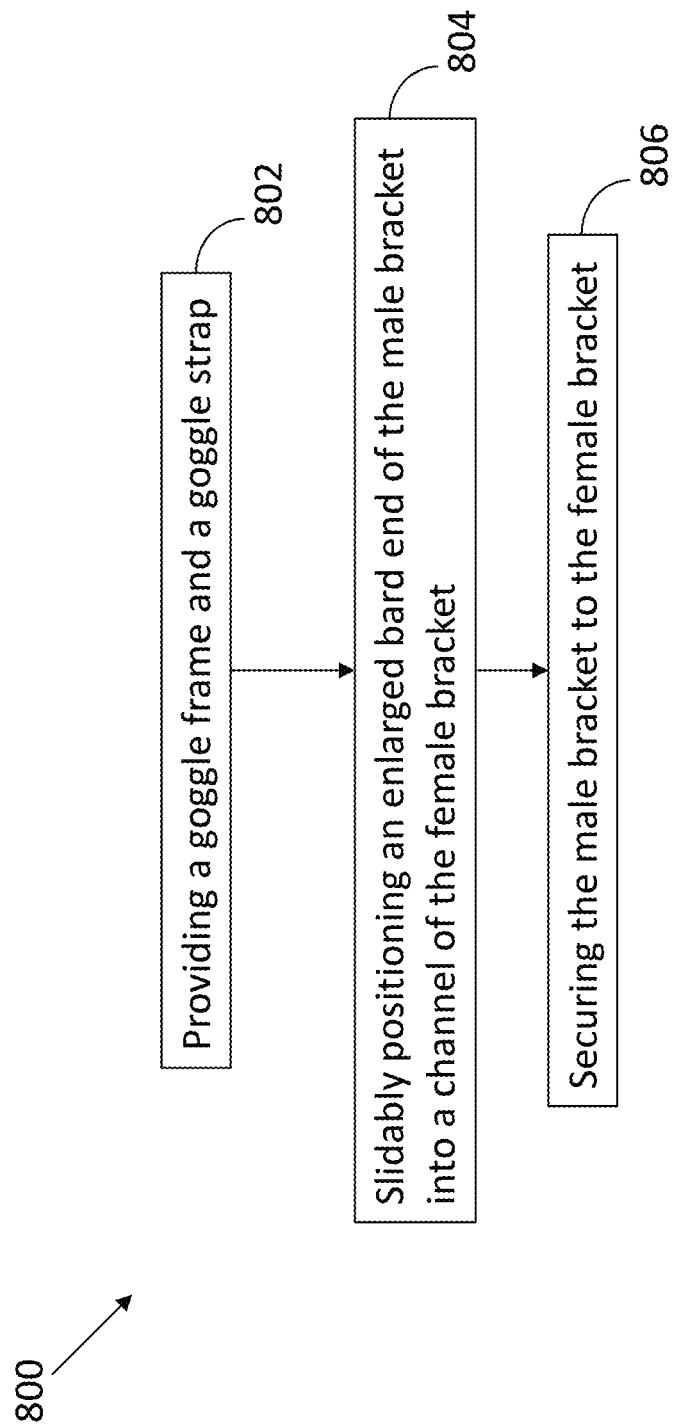
FIG. 8 is a flow chart of a method of coupling a goggle strap to a goggle frame.

Methods of coupling a goggle strap to a goggle frame are also provided herein. FIG. 8 illustrates an example method (800) of coupling a goggle strap to a goggle frame. The method (800) comprises providing a goggle frame and a goggle strap (802). A female bracket is disposed on a first frame side of the goggle frame or a first end of the goggle strap. A male bracket is disposed on the first end of the goggle strap or the first frame side of the goggle frame. The goggle strap has a direction of strap tension when the goggle strap is pulled away from the strap end. The method (800) further comprises slidably positioning an enlarged bar end of the male bracket into a channel of the female bracket through an opening end of the channel by sliding the enlarged bar end into the channel in a direction substantially perpendicular to the direction of strap tension (804). Substantially perpendicular in this application means that the angle between the sliding direction of the enlarged bar end into the channel and the direction of strap tension need not be exactly 90°, but also includes a range of 15° above and below 90° to account for differences in manufacturing and that the angle does not need to be exactly 90° for optimal functionality. The method further comprises securing the male bracket to the female bracket by pulling the male bracket or the female bracket substantially parallel to the direction of strap tension after enlarged bar end is positioned within the channel (806). Substantially parallel in this application means that the difference between the pulling direction of the male bracket or the female bracket and the direction of strap tension need not be exactly 0°, but includes a range of 15° above and below 0° to account for differences in manufacturing and that the angle does not need to be exactly 0° for optimal functionality.

In some embodiments, securing the male bracket to the female bracket further comprises moving one or more bar bumps of the enlarged bar end past one or more projections of the female bracket, and positioning the one or more bar bumps within the one or more recesses of the female bracket immediately adjacent to the one or more projections. In some embodiments, securing the male bracket to the female bracket further comprises pulling the male bracket or the female bracket until a first click is produced. In some embodiments, the method (800) further comprises unsecuring the male bracket from the female bracket by pushing the male bracket and the female bracket toward each other substantially opposite the direction of strap tension until one or more bar bumps of the enlarged bar end disengages from one or more recesses, and sliding the enlarged bar end out of the channel in a direction substantially perpendicular to the direction of strap tension. In some embodiments, unsecuring the male bracket from the female bracket further comprises pushing the male bracket and the female bracket toward each other until a second click is produced. In some embodiments, slidably positioning the enlarged bar end of the male bracket into the channel of the female bracket further comprises slidably positioning the enlarged bar end of the male bracket into the channel of the female bracket until the enlarged bar end reaches a closed end of the channel opposite the opening end of the channel.

This disclosure, its aspects and implementations, are not limited to the specific components or assembly procedures disclosed herein. Many additional components and assembly procedures known in the art consistent with the intended goggles and methods of coupling a goggle strap to a goggle frame will become apparent for use with implementations of the apparatus and methods in this disclosure. In places where the description above refers to particular implementations of goggles, it should be readily apparent that a number of modifications may be made without departing from the spirit thereof and that these implementations may be applied to other goggles. The presently disclosed implementations are, therefore, to be considered in all respects as illustrative and not restrictive, the scope of the disclosure being indicated by the appended claims rather than the foregoing description. All changes that come within the meaning of and range of equivalency of the description are intended to be embraced therein. Accordingly, for example, although particular goggles and methods of coupling a goggle strap to a goggle frame are disclosed, such apparatus, methods, and implementing components may comprise any shape, size, style, type, model, version, class, grade, measurement, concentration, material, quantity, and the like as is known in the art for such apparatus, methods, and implementing components, and/or the like consistent with the intended operation of the goggles and methods of coupling a goggle strap to a goggle frame may be used.

The word "exemplary," "example," or various forms thereof are used herein to mean serving as an example, instance, or illustration. Any aspect or design described herein as "exemplary" or as an "example" is not necessarily to be construed as preferred or advantageous over other aspects or designs. Furthermore, examples are provided solely for purposes of clarity and understanding and are not meant to limit or restrict the disclosed subject matter or relevant portions of this disclosure in any manner. It is to be appreciated that a myriad of additional or alternate examples of varying scope could have been presented, but have been omitted for purposes of brevity.

The invention claimed is:

1. A pair of goggles comprising:
    a goggle frame comprising two frame sides opposite each other, and at least one lens aperture defined by the goggle frame;
    at least one lens mounted on the goggle frame and covering the at least one lens aperture;
    a goggle strap having two strap ends each having a direction of strap tension when the pair of goggles is worn by a user; and
    a goggle strap connector at each of the two frame sides, each goggle strap connector respectively comprising:
        a female bracket coupled to the respective frame side and comprising:
            a first bracket wall and a second bracket wall, each extending away from the respective frame side;
            a channel having a length greater than its width and its height, and formed between the bracket walls, the channel having an opening end with an opening end height and an opening end width;
            one or more projections facing the channel and extending into the channel from the first bracket wall;
            one or more recesses on the first bracket wall immediately adjacent to each of the one or more projections and distal to the respective frame side relative to the one or more projections; and
            an opposing pair of first teeth facing each other and each separately extending toward the respective frame side from a different wall of the first and second bracket walls, the pair of first teeth positioned distal to the respective frame side relative to the one or more recesses on the first bracket wall; and
        a male bracket on each of the two strap ends, each male bracket respectively comprising:
            a strap coupler coupled to one of the two strap ends;
            a sliding bar extending from the strap coupler away from the goggle strap;
            an enlarged bar end disposed on an edge of the sliding bar distal to the strap coupler, the enlarged bar end comprising one or more bar bumps along at least a portion of the edge of the sliding bar; and
            an opposing pair of second teeth facing away from each other and each separately extending from the edge of the sliding bar toward the strap coupler;
        wherein the opening end height and the opening end width of each channel is greater than a corresponding height and a corresponding width of the enlarged bar end to slidably receive the enlarged bar end into the channel, and wherein first movement of the male bracket within the channel in the strap tension direction moves at least one of the one or more bar bumps of the respective enlarged bar end past at least one of the one or more projections of the female bracket to position the at least one of the one or more bar bumps within the at least one of the one or more recesses and engage the pair of first teeth with the pair of second teeth.

2. The pair of goggles of claim 1, wherein the channel comprises a closed end opposite the opening end of the channel.

3. The pair of goggles of claim 1, wherein second movement of the male bracket within the channel in a direction opposite the strap tension direction moves the at least one of the one or more bar bumps out of the at least one of the one or more recesses and past the at least one of the one or more projections.

4. The pair of goggles of claim 3, wherein the first movement of the male bracket produces a first click and the second movement of the male bracket produces a second click.

5. The pair of goggles of claim 1, wherein the one or more bar bumps comprise a first bar bump proximal to the second teeth and a second bar bump disposed distal to the first bar bump on the sliding bar, the one or more projections comprise a first projection proximal to the first teeth and a second projection distal to the opening end of the channel, the one or more recesses comprise a first recess and a second recess, and the enlarged bar end at the second bar bump having a height greater than a height of the channel measured between the first bracket wall and the second bracket wall adjacent to the second recess, but smaller than a height of the channel measured between the first bracket wall and the second bracket wall at the second recess.

6. The pair of goggles of claim 5, wherein the female bracket further comprises a recess wall which extends into the channel from the first bracket wall or the second bracket wall and faces the channel, the recess wall not parallel to the second projection and disposed immediately adjacent to the second recess.

7. A pair of goggles comprising:
    a goggle frame comprising a first frame side;
    a goggle strap having a first strap end, the first strap end having a direction of strap tension when the pair of goggles is worn by a user; and
    a goggle strap connector at the first frame side, the goggle strap connector comprising:
        a female bracket directly coupled to the first frame side or the first strap end and comprising:
            a first bracket wall and a second bracket wall facing each other and joined by a channel base;
            a channel defined between the bracket walls and having a length greater than its width, the channel further having an opening end with an opening end height and an opening end width;
            one or more projections extending into the channel from the first bracket wall;
            one or more recesses on the first bracket wall immediately adjacent to the one or more projections and distal to the channel base relative to the one or more projections; and
        a male bracket configured to mateably couple to the female bracket and comprising:
            a sliding bar comprising a proximal end and a distal end, the proximal end directly coupled to the other of the first frame side or the first strap end that the female bracket is not directly coupled to; and
            an enlarged bar end disposed on the sliding bar at the distal end, the enlarged bar end comprising one or more bar bumps along at least a portion of the sliding bar;
        wherein the opening end height and the opening end width of the channel is greater than a corresponding height and a corresponding width of the enlarged bar end to slidably receive the enlarged bar end into the channel, and wherein first movement of the first strap end in the strap tension direction moves at least one of the one or more bar bumps of the enlarged bar end past at least one of the one or more projections of the female bracket to position the at least one of the one or more bumps within at least one of the one or more recesses and engage the male bracket with the female bracket.

8. The pair of goggles of claim 7, wherein the female bracket comprises an opposing pair of first teeth facing each other and each separately extending toward the channel base from a different wall of the first and second bracket walls, the pair of first teeth positioned distal to the channel base relative to the one or more recesses on the first bracket wall, the male bracket further comprises an opposing pair of second teeth facing away from each other and each separately extending from the enlarged bar end at the distal end of the sliding bar toward the proximal end, and the first movement moves the at least one of the one or more bar bumps of the enlarged bar end past the at least one of the one or more projections to engage the pair of first teeth with the pair of second teeth.

9. The pair of goggles of claim 7, wherein the channel comprises a closed end opposite the opening end of the channel.

10. The pair of goggles of claim 7, wherein second movement of the male bracket within the channel, or the female bracket with the male bracket within the channel, in a direction opposite the strap tension direction moves the at least one of the one or more bumps out of the at least one of the one or more recesses and past the at least one of the one or more projections of the female bracket.

11. The pair of goggles of claim 10, wherein the first movement produces a first click and the second movement produces a second click.

12. The pair of goggles of claim 7, wherein the one or more bar bumps comprise a first bar bump and a second bar bump disposed distal to the first bar bump on the sliding bar, the one or more projections comprise a first projection proximal to the opening end and a second projection distal to the opening end of the channel, the one or more recesses comprise a first recess and a second recess, and the enlarged bar end at the second bar bump having a height greater than a height of the channel measured between the first bracket wall and the second bracket wall adjacent to the second recess, but smaller than a height of the channel measured between the first bracket wall and the second bracket wall at the second recess.

13. The pair of goggles of claim 12, wherein the first bar bump is proximal to a pair of second teeth and the first projection is proximal to a pair of first teeth.

14. The pair of goggles of claim 12, wherein the female bracket further comprises a recess wall which extends into the channel from the first bracket wall or the second bracket wall and faces the channel, the recess wall not parallel to the second projection and disposed immediately adjacent to the second recess.

15. A method of coupling a goggle strap to a goggle frame, the method comprising:
prov150ing a goggle frame and a goggle strap, a female bracket disposed on a first frame side of the goggle frame or a first end of the goggle strap, and a male bracket disposed on the first end of the goggle strap or the first frame side of the goggle frame, wherein the goggle strap having a direction of strap tension when the goggle strap is pulled away from the strap end;
slidably positioning an enlarged bar end of the male bracket into a channel of the female bracket through an opening end of the channel by sliding the enlarged bar end into the channel in a direction substantially perpendicular to the direction of strap tension; and
securing the male bracket to the female bracket by pulling the male bracket or the female bracket substantially parallel to the direction of strap tension after the enlarged bar end is positioned within the channel;
wherein securing the male bracket to the female bracket further comprises pulling the male bracket or the female bracket until a first click is produced.

16. The method of claim 15, wherein securing the male bracket to the female bracket further comprises moving one or more bar bumps of the enlarged bar end past one or more projections of the female bracket, and positioning the one or more bar bumps within the one or more recesses of the female bracket immediately adjacent to the one or more projections.

17. The method of claim 15, further comprising unsecuring the male bracket from the female bracket by pushing the male bracket and the female bracket toward each other opposite the direction of strap tension until one or more bar bumps of the enlarged bar end disengage from one or more recesses, and sliding the enlarged bar end out of the channel in a direction substantially perpendicular to the direction of strap tension.

18. The method of claim 17, wherein unsecuring the male bracket from the female bracket further comprises pushing the male bracket and the female bracket toward each other until a second click is produced.

19. The method of claim 15, wherein slidably positioning the enlarged bar end of the male bracket into the channel of the female bracket further comprises slidably positioning the enlarged bar end of the male bracket into the channel of the female bracket until the enlarged bar end reaches a closed end of the channel opposite the opening end of the channel.

* * * * *